US00PP22555P2

(12) United States Plant Patent
Zerr

(10) Patent No.: US PP22,555 P2
(45) Date of Patent: Mar. 6, 2012

(54) *POINSETTIA* PLANT NAMED 'SYEP23203'

(50) Latin Name: *Euphorbia pulcherrima*
Varietal Denomination: SYEP23203

(75) Inventor: Katharina Zerr, Hillscheid (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/932,413

(22) Filed: Feb. 24, 2011

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell

(74) *Attorney, Agent, or Firm* — S. Matthew Edwards

(57) ABSTRACT

A new *Poinsettia* plant named 'SYEP23203' particularly distinguished by relatively medium to large inflorescences, with wide, horizontally borne bracts, brilliant red bract color, dark green foliage, leaves with weak lobing, good branching v-shaped, upright plant habit with strong stems, mid season flowering in normal culture, but also suitable for early crops.

1 Drawing Sheet

Latin name of the genus and species of the plant claimed: *Euphorbia pulcherrima.*

Varietal denomination: 'SYEP23203'.

BACKGROUND OF THE NEW PLANT

The present invention comprises a new *Poinsettia* plant, botanically known as *Euphorbia pulcherrima*, and hereinafter referred to by the variety name 'SYEP23203'.

'SYEP23203' is a product of a planned breeding program. The new cultivar 'SYEP23203' has brilliant red bract color, wide, ovate bract shape, dark green foliage with only weak lobing, mid season flowering, and v-shaped upright plant habit with strong stems.

'SYEP23203' originated from a hybridization made in the summer of 2003 in a controlled breeding program in Hillscheid, Germany. The female parent was the proprietary variety 'S90-1901-1', not patented, with intense red colored bracts, medium-green foliage, medium to tall plant habit and relatively late flowering.

The male parent of 'SYEP23203' was the proprietary plant 'Fispoin 7776', not patented. 'Fispoin 7776' was applied for with the PBR authority in Canada but was withdrawn when it became clear that the variety would not be introduced and marketed. 'Fispoin 7776' has large, red to slightly orange-red bracts, dark green foliage with distinct lobes, and medium sized plant habit with relatively upright directed stems.

The resulting seeds were sown in February to March 2004 and 'SYEP23203' was selected as one flowering plant within the progeny of the stated cross in December 2004 during a greenhouse trial cultivation in Hillscheid, Germany.

The first act of asexual reproduction of 'SYEP23203' was accomplished when shoot-tips were cut for the cultivation of single-stem plants in the summer of 2004 for the above greenhouse trial.

In April through May 2005 shoot-tips were cut once more to be grafted onto rootstocks of the variety 'Maren' in order to improve the branching ability. Cuttings from the successfully grafted stems were used in the summer of 2007, rooted and cultivated as branched plants for a small trial in fall and winter of 2007.

Horticultural examination of plants grown from cuttings of the plant initiated in the summer of 2007 in Hillscheid, Germany, and continuing thereafter on a larger scale, has demonstrated that the combination of characteristics as herein disclosed for 'SYEP23203' are firmly fixed and are retained through successive generations of asexual reproduction.

A Plant Breeder's Right for this cultivar has been applied for in Switzerland in early February 2011. A Plant Breeder's Right has also been applied for in Canada on Mar. 8, 2010 (No. 10-6882). 'SYEP23203' has not been made publicly available more than one year prior to the filing of this application.

'SYEP23203' has not been observed under all possible environmental conditions. The phenotype may vary significantly with variations in environment such as temperature, light intensity and day length

DESCRIPTION OF DRAWING

The accompanying photographic drawings show typical flower and foliage characteristics of 'SYEP23203' with colors being as true as possible with an illustration of this type.

DETAILED BOTANICAL DESCRIPTION

Figure 1:
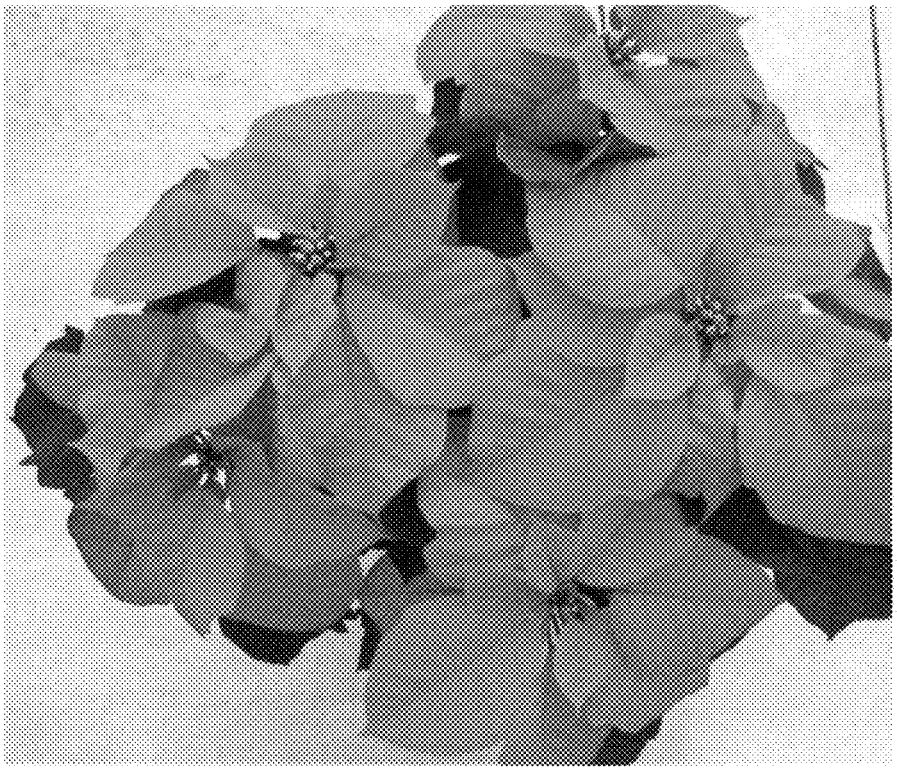
FIG. 1 is a top view of an 18 week old flowering plant taken at Monroeville, N.J., on Dec. 3, 2010.
Figure 2:
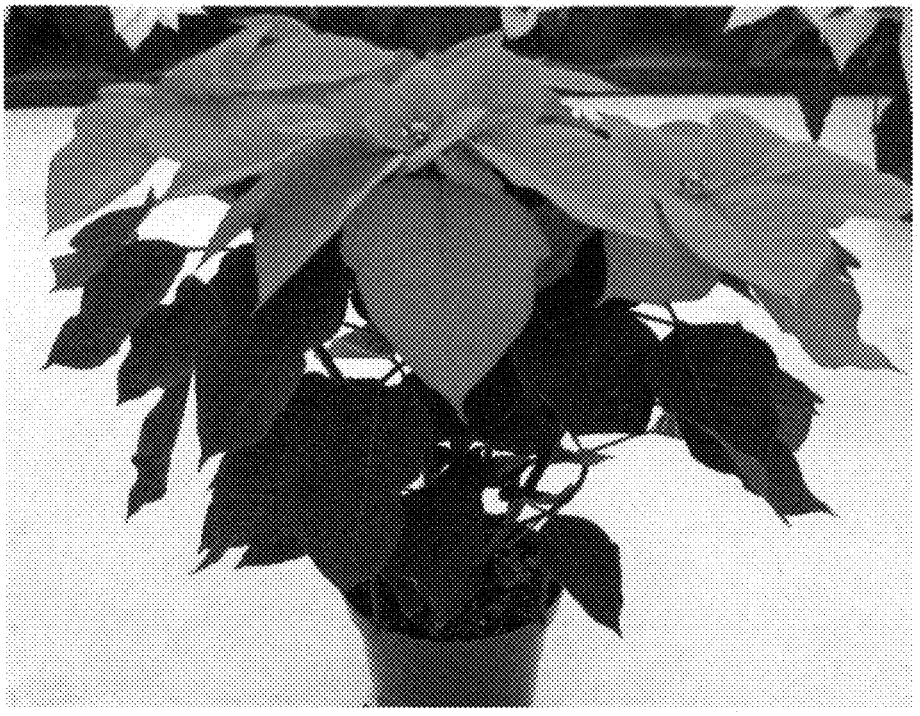
FIG. 2 is a side view taken 2 weeks earlier in the same place.

The measurements were taken in Enkhuizen, The Netherlands, on Dec. 16, 2010 on about 18 week old plants growing in a greenhouse. Culture of these plants had started on Aug. 10, 2010 with planting rooted cuttings into 12 cm pots and pinching the plants two weeks later. Cultivation was under natural day light in the fall (no applying of black cloth to initiate earlier flowering) and at 18-20° C. temperature for the bench heating.

Color Chart used: Royal Horticultural Society Colour Chart (R.H.S.) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this *Poinsettia* plant as a new and distinct variety.

1. Brilliant red flower bract color,
2. Broad ovate bracts, somewhat rugose
3. Relatively large inflorescences, with the bracts borne horizontally
4. Dark green foliage, leaves with weak lobes
5. Strong stems, relatively upright, v-shaped plant habit
6. About medium vigor, well branching
7. Medium/mid season flowering response
8. Good tolerance to cool cultivation temperature,
9. Suitable for early crops as there is little heat delay

TABLE 1

DIFFERENCES BETWEEN THE NEW VARIETY 'SYEP23203' AND SIMILAR VARIETIES

| | | 'SYEP23203' |
|---|---|---|
| | 'FISMARS' (U.S. Plant Pat. No. 14,977) | |
| Bract color | Intermediate between RHS 46B and 46C | More orange-red than RHS 45B |
| Diameter of inflorescences | 22.8 cm | 23.7 cm (slightly larger) |
| Width of bracts | 7.9 cm | 8.8 cm |
| Plant height | 26.2 cm | 29 cm |
| | 'ECKADIRE' (U.S. Plant Pat. No. 12,846) | |
| Bract color | RHS 46B | More orange-red than RHS 45B |
| Bract shape and aspect | Ovate, relatively narrower in shape, slanting upright | Wider, ovate, borne horizontally |
| Heat delay (delayed flowering in early crops due to high temperature) | Moderate to distinct | Little |

Plant:

*Form, growth and habit.*—Shrub, uprights plant habit, with the branches relatively steep at an angle of over 45 degrees, and well-branched.

*Plant height* (*without pot*).—29 cm.

*Plant width.*—38.5 cm.

*Number of branches.*—8.66.

*Number of inflorescences.*—8-9.

Root:

*Number of days to produce a rooted cutting/liner/young plant.*—24-25 days at a temperature of 22-24 degrees centigrade.

*Form.*—Self-branching, somewhat fleshy.

*Color.*—Near RHS N155B.

Stem:

*Color of stem.*—Main portion: deep green, RHS 147A, infused with anthocyanin (reddish tones), RHS 181A, fading towards the tip; top portion of stem approximately RHS 137C.

*Length of stem.*—Approximately 20-25 cm.

*Diameter.*—0.5-0.7 cm.

*Length of internodes.*—1.5-2.5 cm.

*Texture.*—Smooth, glabrous.

Foliage:

*Arrangement.*—Alternate.

*Quantity.*—5-7 leaves per branch.

*Aspect.*—Petioles are horizontally to slightly ascending, while the leaf blades usually somewhat show downwards.

*Growing leaves* (*when plant in vegetative stage*), *color upper surface.*—RHS 143A.

*Growing leaves, color lower surface.*—RHS 137D.

*Mature leaves, color, upper surface.*—Dark green, intermediate between the tones of RHS 137A and 139A, or near RHS 139A.

*Mature leaves, color lower surface.*—RHS 137C.

*Leaf length.*—10.75 cm.

*Leaf width.*—8.25 cm.

*Shape.*—Ovate with a weak, or occasionally weak to medium, degree of lobing.

*Base shape.*—Obtuse.

*Apex shape.*—Acuminate.

*Margin.*—Entire, the lobes have usually rounded tips.

*Texture.*—Flat, smooth, apart from the protruding veins on the underside; under side with very short, fine hair, while the upper surface appears glabrous.

*Venation pattern.*—Pinnate.

*Color of veins, upper surface.*—Approximately RHS 53C at base, fading and turning indistinct towards tip.

*Color of veins, lower surface.*—RHS 184D.

*Petiole color, upper surface.*—Deep purple, RHS 60A.

*Petiole color, lower surface.*—RHS 181A to 181B.

*Petiole length.*—About 6-7 cm.

*Diameter of petiole.*—2.5-3 mm.

*Texture upper and lower surfaces.*—Smooth, glabrous.

Inflorescence:

*Type.*—Terminal cyme with surrounding whorl of colored Flower bracts.

*Flowering, botanically* (*opening of the stamina, shedding of pollen*).—When grown under natural short day in fall: In early December.

*Flowering period, commercially* (*sufficiently colored bracts*).—From late November.

*Flowering response time.*—9-10 weeks from equinox.

*Duration of flowering.*—Depends from light and environment, at least 4-8 weeks of 'shelf' life.

*Fragrance.*—Absent.

*Shape of inflorescence.*—Rosette-like arrangement, the larger bracts are mostly flat, borne horizontally and overlapping.

*Diameter of inflorescence.*—23.7 cm.

*Inflorescence, vertical diameter.*—Approximately 4 cm.

*Number of completely colored bracts per inflorescence* (*sized over 2 cm*).—10-14.

*Single bract, shape.*—Ovate, weakly oak-shaped (that is, has weak lobes).

*Bract, apex.*—Acuminate.

*Bract, base.*—Rounded to obtuse.

*Margin.*—Entire.

*Single bract, length of blade.*—12.1 cm, younger bracts diminishing in size.

*Single bract, width of blade.*—8.8 cm.

*Bract color, upper side.*—A slightly more orange-red hue than RHS 45B.

*Bract color, lower side.*—Near RHS 46D or closer to RHS 53D.

*Venation pattern.*—Pinnate.

*Vein color, upper surface.*—RHS 51B at base, indistinct towards the tip.

*Vein color, lower surface*.—RHS 181C near base, fading to cream towards tip (RHS 159A).

*Bract petiole length*.—1.8-2.5 cm, shorter for the younger bracts.

*Bract petiole diameter*.—2-2.5 mm.

*Petiole color, upper surface*.—Between RHS 46A and 46B.

*Petiole color, lower surface*.—Approximately RHS 47C or 180B.

*Texture*.—Somewhat wrinkled, glabrous.

Cyme (true inflorescence):

*Cyme, diameter*.—Relatively small, approximately 1.5-2 cm.

*Number of cyathia*.—Most often 1-5, borne in a tight cluster.

*Cyathium, shape*.—Ovate.

*Cyathium, diameter*.—0.6 cm.

*Cyathium, length*.—0.6-0.7 cm.

*Color*.—Mainly RHS 143C, top is RHS 46C.

*Peduncle length*.—2-3 mm.

*Peduncle color*.—RHS 144B.

*Nectar cups*.—Usually one per cyathium.

*Nectur cup, width*.—Mostly 5-6 mm.

*Nectar cup, color*.—Deep yellow, RHS 13C.

Reproductive organs:

*Stamen* (*actually reduced male florets*).—Usually in a bunch of 15-20 at the top of the cyathium.

*Shape*.—Strap-like.

*Filament length*.—2 mm.

*Filament color*.—Red, RHS 46B.

*Anther color*.—Yellow, RHS 11A.

*Anther diameter*.—1 mm.

*Pollen quantity*.—Moderate (normal quantity).

*Pollen color*.—RHS 12A.

*Pistils* (*actually female flowers*).—Not observed in Enkhuizen.

*Fertility/seed set*.—No seed set observed.

Disease/pest resistance: Disease resistance or susceptibility has not been observed on this hybrid.

What is claimed is:

1. A new and distinct variety of *Poinsettia* plant named 'SYEP23203', substantially as illustrated and described herein.

* * * * *